United States Patent
Turnlund et al.

(10) Patent No.: US 9,808,595 B2
(45) Date of Patent: Nov. 7, 2017

(54) MICROFABRICATED CATHETER WITH IMPROVED BONDING STRUCTURE

(75) Inventors: Todd H. Turnlund, Park City, UT (US); Walter Lynn Kerby, South Jordan, UT (US)

(73) Assignee: BOSTON SCIENTIFIC SCIMED, INC, Maple Grove, MN (US)

( * ) Notice: Subject to any disclaimer, the term of this patent is extended or adjusted under 35 U.S.C. 154(b) by 1230 days.

(21) Appl. No.: 11/835,207

(22) Filed: Aug. 7, 2007

(65) Prior Publication Data

US 2009/0043283 A1 Feb. 12, 2009

(51) Int. Cl.
*A61M 25/00* (2006.01)
*A61M 25/01* (2006.01)

(52) U.S. Cl.
CPC .... *A61M 25/0013* (2013.01); *A61M 25/0051* (2013.01); *A61M 25/0054* (2013.01); *A61M 25/0045* (2013.01); *A61M 25/0138* (2013.01); *A61M 2025/006* (2013.01); *A61M 2025/0006* (2013.01)

(58) Field of Classification Search
CPC .......... A61M 25/0013; A61M 25/0051; A61M 25/0054; A61M 25/0138; A61M 25/0144; A61M 2025/0006; A61M 2025/006; A61M 25/0053; A61M 2025/0161; A61M 25/005; A61M 25/0012; A61M 2025/0004
USPC ............ 604/523–525, 95.03, 95.04; 600/585
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Bhisma Mehta
*Assistant Examiner* — Larry R Wilson
(74) *Attorney, Agent, or Firm* — Seager, Tufte & Wickhem, LLP

(57) ABSTRACT

Medical devices and methods for making and using the same. An example medical device may include a tubular member and a liner disposed within the tubular member. The tubular member may have a plurality of slots formed therein. A space may be defined between the tubular member and the liner. One or more bonding members may be disposed in the space.

22 Claims, 8 Drawing Sheets

(56) References Cited

U.S. PATENT DOCUMENTS

| | | |
|---|---|---|
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,516,972 A | 5/1985 | Samson |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,981,478 A | 1/1991 | Evard et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gambale |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,176,660 A | 1/1993 | Truckai |
| 5,180,376 A | 1/1993 | Fischell |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,454,795 A * | 10/1995 | Samson ............... A61L 29/041 600/435 |
| 5,458,605 A | 10/1995 | Klemm |
| 5,460,187 A | 10/1995 | Daigle et al. |
| 5,460,608 A | 10/1995 | Lodin et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |

(56) References Cited

U.S. PATENT DOCUMENTS

| | | |
|---|---|---|
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,603,705 A | 2/1997 | Berg |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,674,208 A | 10/1997 | Berg et al. |
| 5,676,659 A | 10/1997 | McGurk |
| 5,676,697 A | 10/1997 | McDonald |
| 5,680,873 A | 10/1997 | Berg et al. |
| 5,682,894 A | 11/1997 | Orr et al. |
| 5,690,120 A | 11/1997 | Jacobsen et al. |
| 5,702,373 A | 12/1997 | Samson |
| 5,720,300 A | 2/1998 | Fagan et al. |
| 5,722,609 A | 3/1998 | Murakami |
| 5,728,063 A | 3/1998 | Preissman et al. |
| 5,733,248 A | 3/1998 | Adams et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,830,155 A | 11/1998 | Frechette et al. |
| 5,833,631 A | 11/1998 | Nguyen |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,853,400 A | 12/1998 | Samson |
| 5,860,963 A | 1/1999 | Azam et al. |
| 5,891,114 A | 4/1999 | Chien et al. |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 5,980,471 A | 11/1999 | Jafari |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,053,903 A | 4/2000 | Samson |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,152,912 A | 11/2000 | Jansen et al. |
| 6,159,187 A | 12/2000 | Park et al. |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,212,422 B1 | 4/2001 | Berg et al. |
| 6,214,042 B1 | 4/2001 | Jacobsen et al. |
| 6,228,073 B1 | 5/2001 | Noone et al. |
| 6,240,231 B1 | 5/2001 | Ferrera et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,508,806 B1 | 1/2003 | Hoste |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 | 6/2003 | Jacobsen et al. |
| 6,602,207 B1 | 8/2003 | Mann et al. |
| 6,602,280 B2 | 8/2003 | Chobotov |
| 6,610,046 B1 | 8/2003 | Usami et al. |
| 6,623,448 B2 | 9/2003 | Slater |

(56) References Cited

U.S. PATENT DOCUMENTS

| | | | |
|---|---|---|---|
| 6,636,758 | B2 | 10/2003 | Sanchez et al. |
| 6,638,266 | B2 | 10/2003 | Wilson et al. |
| 6,652,508 | B2 | 11/2003 | Griffin et al. |
| 6,682,493 | B2 | 1/2004 | Mirigian |
| 6,689,120 | B1 | 2/2004 | Gerdts |
| 6,702,762 | B2 | 3/2004 | Jafari et al. |
| 6,712,826 | B2 | 3/2004 | Lui |
| 6,730,095 | B2 | 5/2004 | Olson, Jr. et al. |
| 6,746,422 | B1* | 6/2004 | Noriega ............ A61M 25/0138 604/95.05 |
| 6,749,560 | B1 | 6/2004 | Konstorum et al. |
| 6,766,720 | B1 | 7/2004 | Jacobsen et al. |
| 6,777,644 | B2 | 8/2004 | Peacock, III et al. |
| 6,811,544 | B2 | 11/2004 | Schaer |
| 6,837,898 | B2 | 1/2005 | Boyle et al. |
| 6,866,642 | B2 | 3/2005 | Kellerman et al. |
| 6,866,665 | B2 | 3/2005 | Orbay |
| 6,887,235 | B2 | 5/2005 | O'Connor et al. |
| 6,896,671 | B2 | 5/2005 | Vitullo et al. |
| 6,918,882 | B2 | 7/2005 | Skujins et al. |
| 6,997,937 | B2 | 2/2006 | Jacobsen et al. |
| 7,001,369 | B2 | 2/2006 | Griffin et al. |
| 7,074,197 | B2 | 7/2006 | Reynolds et al. |
| 7,153,277 | B2 | 12/2006 | Skujins et al. |
| 7,182,735 | B2 | 2/2007 | Shireman et al. |
| 7,850,623 | B2* | 12/2010 | Griffin .............. A61M 25/0013 600/585 |
| 2002/0013540 | A1 | 1/2002 | Jacobsen et al. |
| 2002/0019599 | A1 | 2/2002 | Rooney et al. |
| 2003/0009208 | A1 | 1/2003 | Snyder et al. |
| 2003/0060732 | A1 | 3/2003 | Jacobsen et al. |
| 2003/0069522 | A1* | 4/2003 | Jacobsen ........... A61M 25/0013 600/585 |
| 2003/0216668 | A1 | 11/2003 | Howland et al. |
| 2004/0045645 | A1 | 3/2004 | Zhou |
| 2004/0082879 | A1* | 4/2004 | Klint ................ A61B 17/12022 600/585 |
| 2004/0116831 | A1 | 6/2004 | Vrba |
| 2004/0142643 | A1 | 7/2004 | Miller et al. |
| 2004/0167436 | A1 | 8/2004 | Reynolds et al. |
| 2004/0167437 | A1 | 8/2004 | Sharrow et al. |
| 2004/0167440 | A1 | 8/2004 | Sharrow |
| 2004/0167441 | A1 | 8/2004 | Reynolds et al. |
| 2004/0181174 | A2* | 9/2004 | Davis et al. .................. 600/585 |
| 2004/0181176 | A1 | 9/2004 | Jafari et al. |
| 2004/0181207 | A1 | 9/2004 | Vitullo et al. |
| 2004/0193140 | A1 | 9/2004 | Griffin et al. |
| 2005/0027309 | A1 | 2/2005 | Shiber |
| 2005/0177073 | A1 | 8/2005 | Shiber |
| 2005/0288628 | A1 | 12/2005 | Jordan et al. |
| 2006/0111649 | A1 | 5/2006 | Zhou |
| 2006/0121218 | A1 | 6/2006 | Obara et al. |
| 2006/0122537 | A1 | 6/2006 | Reynolds et al. |
| 2006/0189896 | A1 | 8/2006 | Davis et al. |
| 2006/0264904 | A1 | 11/2006 | Kerby et al. |
| 2007/0100285 | A1 | 5/2007 | Griffin et al. |
| 2007/0100424 | A1 | 5/2007 | Chew et al. |
| 2008/0021347 | A1 | 1/2008 | Jacobsen et al. |
| 2008/0021348 | A1 | 1/2008 | Jacobsen et al. |
| 2008/0021400 | A1 | 1/2008 | Jacobsen et al. |
| 2008/0021401 | A1 | 1/2008 | Jacobsen et al. |
| 2008/0021402 | A1 | 1/2008 | Jacobsen et al. |
| 2008/0021403 | A1 | 1/2008 | Jacobsen et al. |
| 2008/0021404 | A1 | 1/2008 | Jacobsen et al. |
| 2008/0021405 | A1 | 1/2008 | Jacobsen et al. |
| 2008/0021406 | A1 | 1/2008 | Jacobsen et al. |
| 2008/0021407 | A1 | 1/2008 | Jacobsen et al. |
| 2008/0021408 | A1 | 1/2008 | Jacobsen et al. |
| 2008/0077119 | A1 | 3/2008 | Snyder et al. |

FOREIGN PATENT DOCUMENTS

| | | |
|---|---|---|
| BR | 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 823 262 | 2/1998 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| EP | 0215173 | 12/2008 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10328191 | 12/1998 |
| JP | 11-267224 A | 10/1999 |

(56) References Cited

FOREIGN PATENT DOCUMENTS

| | | |
|---|---|---|
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 3325828 | 7/2002 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | 96/38193 | 12/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/45885 | 8/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | 03041783 | 5/2003 |
| WO | 2004012804 | 2/2004 |
| WO | WO 04/012804 | 2/2004 |
| WO | WO 2004/012804 | 2/2004 |
| WO | WO 04/033015 | 4/2004 |
| WO | WO 2004/033015 | 4/2004 |
| WO | 2004047899 | 6/2004 |
| WO | WO 04/093957 | 11/2004 |
| WO | WO 2004/093957 | 11/2004 |
| WO | 2007050718 | 5/2007 |
| WO | 2008/034010 | 3/2008 |

* cited by examiner

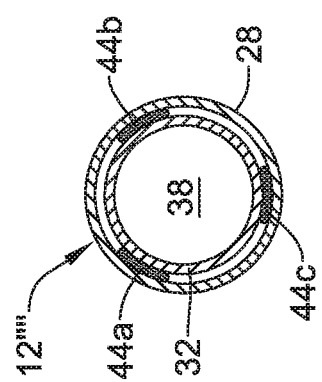

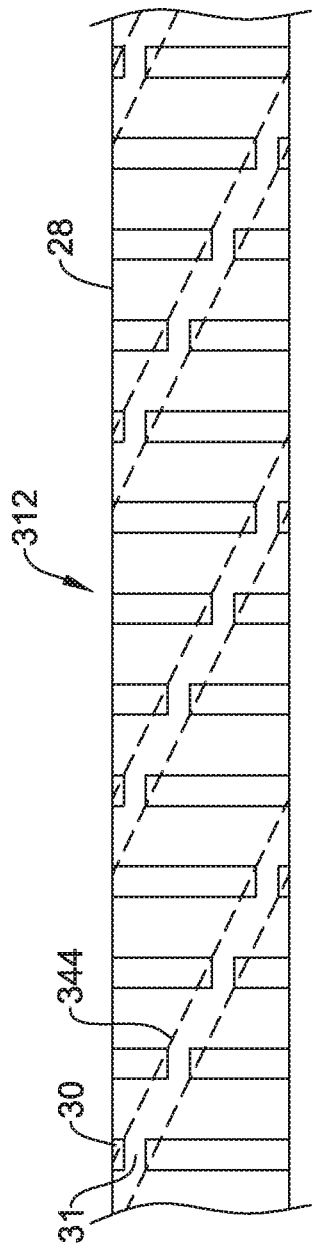
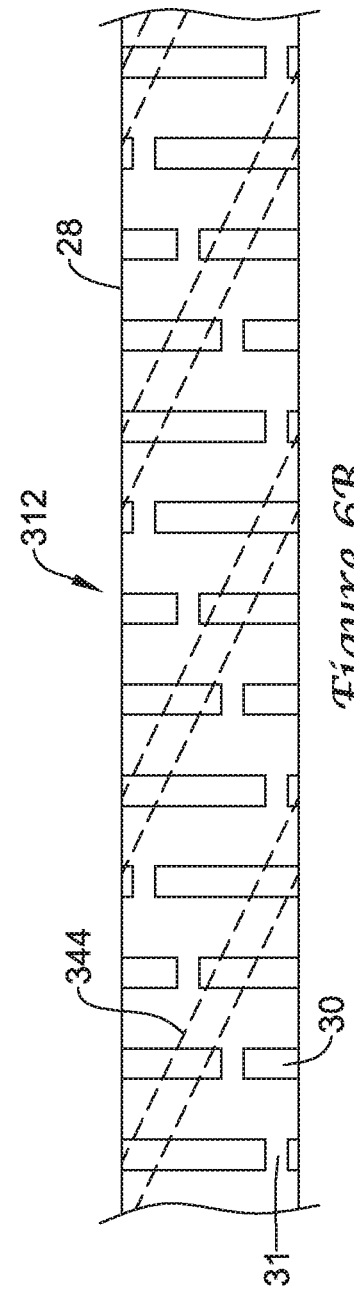

MICROFABRICATED CATHETER WITH IMPROVED BONDING STRUCTURE

CROSS-REFERENCE TO RELATED APPLICATIONS

The application is related to U.S. Pat. No. 7,001,369 and U.S. Patent Application Publication No. US 2006/0264904, the entire disclosures of which are herein incorporated by reference.

FIELD OF THE INVENTION

The present invention pertains to medical devices, and methods for manufacturing medical devices. More particularly, the present invention pertains to medical devices including a tubular member and a liner disposed within the tubular member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices or components thereof. An example medical device may include a tubular member and a liner disposed within the tubular member. The tubular member may have a plurality of slots formed therein. A space may be defined between the inner surface of the tubular member and the outer surface of the liner. One or more bonding members may be disposed in the space to bond the tubular member to the liner.

The above summary of some embodiments is not intended to describe each disclosed embodiment or every implementation of the present invention. The Figures, and Detailed Description, which follow, more particularly exemplify these embodiments

BRIEF DESCRIPTION OF THE DRAWINGS

The invention may be more completely understood in consideration of the following detailed description of various embodiments of the invention in connection with the accompanying drawings, in which:

FIG. 3E is a cross-sectional view of a portion of example medical device;

FIG. 6A is a side view of a portion an example medical device; and

FIG. 6B is a side view of a portion an example medical device.

Figure 1:
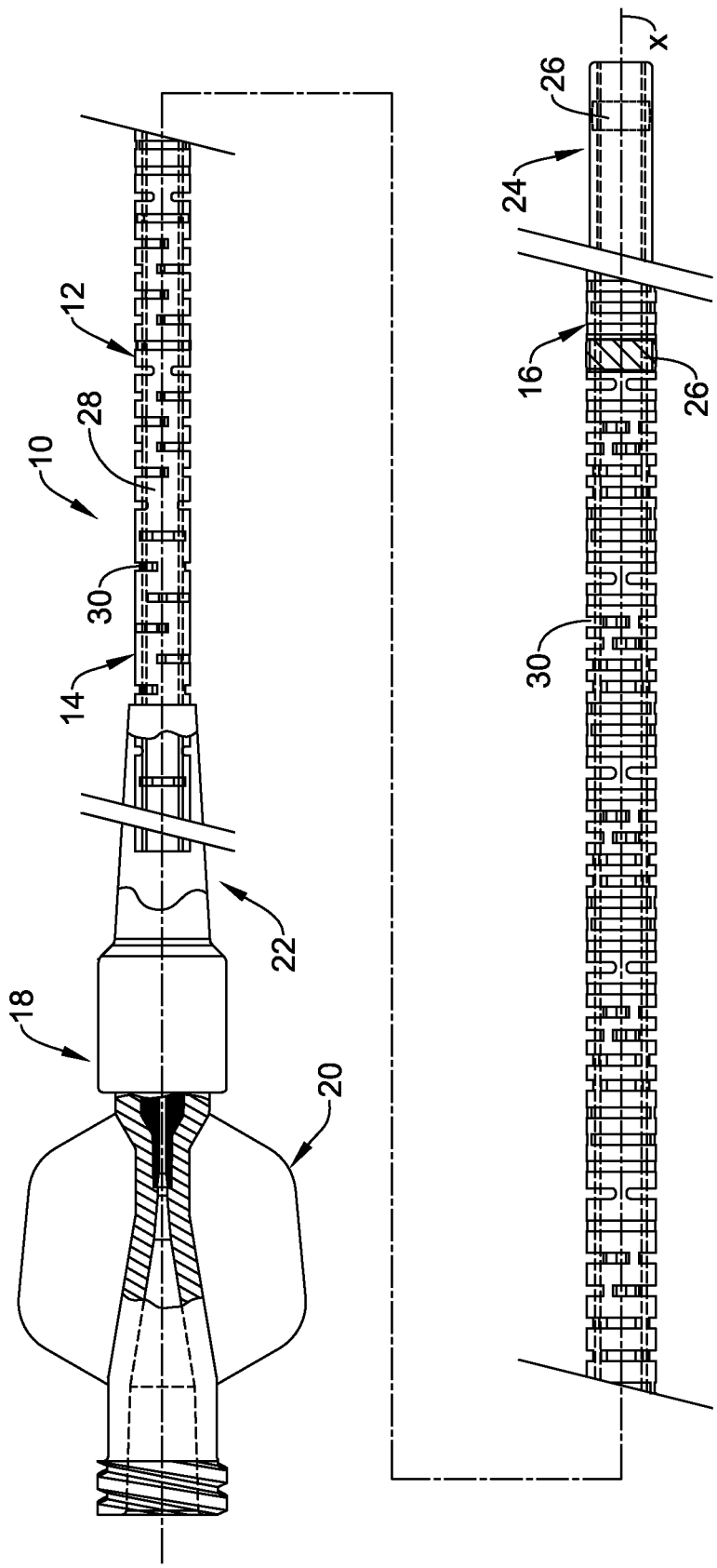
FIG. 1 is a partial cross-sectional side view of an example medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example medical device 10 in the form of a guide catheter. While medical device 10 is depicted as a catheter 10, it should be noted that this is for the purpose of illustration only. Device 10 may take the form of another medical device such as a catheter, a balloon catheter, an atherectomy catheter, a drug delivery catheter, a stent delivery catheter, a microcatheter, an endoscope, an introducer sheath, a fluid delivery device, other infusion or aspiration devices, device delivery (i.e. implantation) devices, and the like. In addition, device 10 may find utility in a variety of different procedures and at a variety of different target locations including blood vessels (coronary, peripheral, neurological, etc.), the digestive tract, the cerebral spinal space, and the like, or any other suitable location.

Catheter 10 may include a generally elongate shaft 12 having a longitudinal axis X, a proximal portion 14, and a distal portion 16. A proximal manifold 18 may be disposed at proximal portion 14. Manifold 18 may include a hub 20 and strain relief 22. A tip member 24 may be disposed at distal portion 16. Tip member 24 may include a radiopaque marker member 26. One or more additional marker members 26 may be disposed along other portions of catheter 10, for example along distal portion 16 of shaft 12. Shaft 12 may include a tubular member 28 having a plurality of slots 30 formed therein. Tubular member 28 may extend along the entire length of shaft 12 or any suitable portion of the length of shaft 12. Likewise, slots 30 may be disposed along a portion or all of tubular member 28. Some additional details regarding tubular member 28 and slots 30 can be found below.

Figure 2:
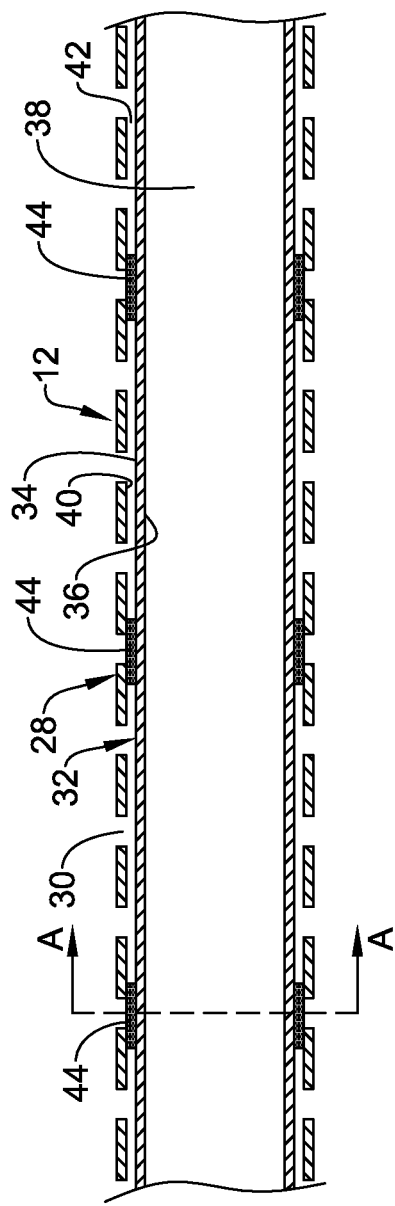
FIG. 2 is longitudinal cross-sectional side view of a portion of the example medical device shown in FIG. 1.

Turning now to FIG. 2, here it can be seen that a tubular liner 32 may be disposed within tubular member 28. Liner 32 may have a length, an outer surface 34, and an inner surface 36. Inner surface 36 may define a lumen 38 that may be, for example, a guidewire lumen or other lumen for catheter 10. Liner 32 may extend along all or a portion of the length of tubular member 28. In some embodiments, liner 32 may extend distally out from tubular member 28 and form tip 24. In other embodiments, tip 24 and liner 32 may be distinct structures.

Liner 32 may generally comprise a polymeric material. Some examples of suitable polymeric materials are listed below. The polymeric material may be selected so as to provide inner surface 36 with the desired amount of lubricity so that devices (e.g., guidewires, etc.) can be manipulated within lumen 38. In some embodiments, liner 32 may be single layer of material. In other embodiments, liner 32 may include a plurality of layers. For example, liner 32 may include an inner layer, an intermediate layer disposed about the inner layer, a reinforcing layer disposed about the intermediate layer, and an outer layer disposed about the reinforcing layer and the intermediate layer. It should be understood that more or fewer layers can be used, with or without one or more reinforcing layers, depending upon the desired characteristics of liner 32. Additionally, in other embodiments, the layers could be arranged differently to achieve desired properties.

In general, along at least a portion of the length of liner 32, outer surface 34 is spaced apart from an inner surface 40 of tubular member 28. In some embodiments, liner 32 is spaced apart from tubular member 28 along the entire length of liner 32. The spacing may define a void or space 42 between the outer surface 34 of liner 32 and the inner surface 40 of tubular member 28. Space 42 may be generally cylindrical in shape, annular in shape, or have any other suitable shape and, as such, it can have or otherwise define a volume.

One or more bonding members 44 may be disposed in space 42. In some embodiments, bonding members 44 are distinct structural elements (e.g., distinct from liner 32 and tubular member 28) that are disposed in space 42. For example, bonding member 44 may include an adhesive, solder, epoxy, a bonding substance, or the like, or any other suitable substance. Alternatively, bonding member 44 may reflect a bonding pattern or bonding region where a portion of liner 32 and/or tubular member 28 extends into space 42 as the result of a bonding procedure. For example, a bonding procedure such as welding, brazing, crimping, heat treating, or the like, or any other suitable procedure may cause a portion of liner 32 (and/or tubular member 28) to extend into space 42 (e.g., liner 32 may partially melt and extend into space 42 and contact tubular member 28) so as to define a bonding member 44. This later "bonding member" 44, in addition to being termed a bonding member, may be equally described as a bonding pattern, bonding configuration, bonding arrangement, etc. Regardless of whether or not bonding member 44 is a distinct structural element or not, the term "bonding member" 44, as used in this disclosure, is understood to mean either of the general configurations described above (i.e., distinct structural element or bonding pattern), to the extent applicable. Furthermore, even though bonding members 44 are depicted as distinct structural elements in the figures, they are not intended to being limit as such as they may actually be either configuration. Consequently, any of the illustrations of bonding member herein may be understood to be structurally-distinct bonding members or bonding members that represent a bonding pattern, bonding configuration, bonding arrangement, etc.

Bonding members 44 may contact and attach outer surface 34 of liner 32 with inner surface 40 of tubular member 28. In addition to attaching liner 32 to tubular member 28, bonding member 44 may have other desirable attributes. For example, bonding member 44 may comprise points of contact between tubular member 28 and liner 32 so that forces (e.g., torsional forces) can be transferred between tubular member 28 and liner 32. This may allow tubular member 28 and liner 32 to perform their respective functions more in unity with one another.

In general, bonding member 44 are arranged so that they occupy a certain amount or portion of the volume defined by space 42. In some embodiments, bonding members 44, in combination, may occupy 50% or more of the volume. In other embodiments, bonding members 44, in combination, may occupy 50% or less of the volume. In still other embodiments, bonding members 44, in combination, may occupy 40% or less of the volume. In still other embodiments, bonding members 44, in combination, may occupy 30% or less of the volume. In still other embodiments, bonding members 44, in combination, may occupy 20% or less of the volume. In still other embodiments, bonding members 44, in combination, may occupy 10% or less of the volume. In some embodiments, it may be desirable for bonding members 44, in combination, to occupy as little of the volume of space 42 as possible while still allowing for tubular member 28 and liner 32 to function in a desirable manner and so that they satisfactorily perform their intended function.

Figure 3B:
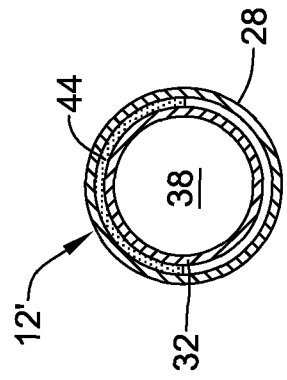
FIG. 3B is a cross-sectional view of an alternative embodiment.

The arrangement and configuration of bonding members 44 relative to liner 32 may also vary. For example, in some embodiments, bonding members 44 may extend circumferentially about (e.g., a complete 360 degrees) liner 32 as shown in FIG. 3A. In other embodiments, bonding members 44 may extend only partially circumferentially about (e.g., less than 360 degrees) a portion of liner 32. For example, FIG. 3B illustrates a portion of another shaft 12', which may be similar in form and function to other shafts disclosed herein, where bonding members 44 extends about half way about the circumference of liner 32. It can be appreciated that embodiments are contemplated where bonding members 44 span all or any suitable portion of the circumference of liner 32 (e.g., ranging anywhere up to 360 degrees). In some embodiments, all of the bonding members 44 extend about the same portion, or all, of the circumference of liner 32. In other embodiments, some of the bonding members 44 extend about different portions of the circumference of liner 32. Various catheters 10 are contemplated that include various arrangements of bonding members 44 including any of those arrangements disclosed herein and/or combinations of the various arrangements disclosed herein.

Figure 3D:
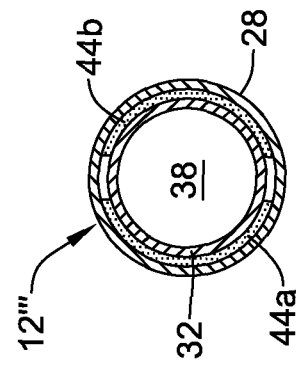
FIG. 3D is a cross-sectional view of an alternative embodiment.
Figure 3A:
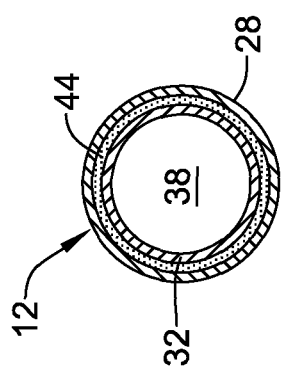
FIG. 3A is a transverse cross-sectional view taken through line A-A of FIG. 2.
Figure 3C:
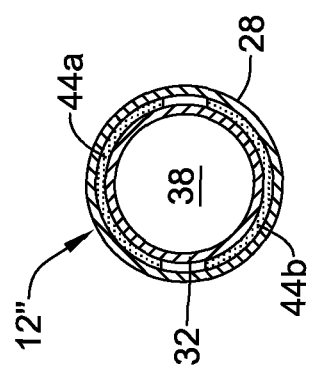
FIG. 3C is a cross-sectional view of an alternative embodiment.

Turning now to FIGS. 3C-3E, here additional example shafts 12"/12'"/12"" are shown where multiple bonding members 44 are disposed at the same longitudinal location along the liner 32. For example, shaft 12" is shown in FIG.

3C with a pair of bonding members 44 disposed opposite one another (e.g., with their centers 180 degrees apart) at the same location along liner 32. Shaft 12''', as shown in FIG. 3D, depicts another pair of bonding members 44 disposed opposite one another at the same location along liner 32. The pair of bonding members 44 in FIG. 3D, however, are rotated relative to the pair of bonding members 44 in FIG. 3C. In FIG. 3E, three bonding members 44a/44b/44c are shown equally spaced about liner 32.

In some embodiments, all of the pairs of bonding members 44 are arranged in the same way so that one of the bonding members 44 from each pair longitudinally aligns. In other embodiments, at least some of the pairs of bonding members 44 are rotated relative to other pairs. For example, some embodiments of catheters 10 include a first pair of bonding members 44 arranged as shown in FIG. 3C and a next adjacent pair spaced longitudinally from the first pair that are rotated relative to the first pair (e.g., arranged as shown in FIG. 3D). The next longitudinally adjacent pair may be rotated like either of the previous two or it may have a different arrangement altogether. It can be appreciated that similar variations are contemplated for groups of bonding members 44 that include 3, 4, 5, 6, or more bonding members 44 disposed at the same longitudinal location along liner 32.

Moreover, when bonding members 44 are arranged in pairs (or otherwise in groups that are disposed at the same longitudinal location), the bonding members 44 may each have the same "length" (i.e., they each extend the same radial distance about liner 32) as depicted in FIGS. 3C and 3D. This, however, need not be the case as numerous catheters are contemplated where pairs or groups of bonding members 44 have different lengths. In addition, the relative lengths of the bonding members 44 in one group may or may not be similar to other groups of bonding members 44.

Furthermore, in some embodiments, all of the groups of bonding members 44 have the same number of bonding members 44. In other embodiments, some of the groups of bonding members 44 have a different number of bonding members 44.

It can be appreciated that a vast array of possibilities exist for the arrangement of bonding members 44 that are within the spirit of the invention.

In some embodiments, the interval or distance between longitudinally adjacent bonding members 44 is fixed along the length of liner 32. For example, in some embodiments, the interval between longitudinally adjacent bonding members is in the range of about 15 centimeters or less, about 14 centimeters or less, about 13 centimeters or less, about 12 centimeters or less, about 11 centimeters or less, about 10 centimeters or less, about 9 centimeters or less, about 8 centimeters or less, about 7 centimeters or less, about 6 centimeters or less, about 5 centimeters or less, about 4 centimeters or less, about 3 centimeters or less, about 2 centimeters or less, about 1 centimeter or less, or any other suitable interval. This interval may be constant or may change along the length of liner 32. In at least some embodiments, at least a portion of the tubular member 28 overlaps with liner 34 and defines an overlapping portion. Along the overlapping portion, there may be at least one bonding member 44 disposed at intervals of about every 15 centimeters or less, about every 14 centimeters or less, about every 13 centimeters or less, about every 12 centimeters or less, about every 11 centimeters or less, about every 10 centimeters or less, about every 9 centimeters or less, about every 8 centimeters or less, about every 7 centimeters or less, about every 6 centimeters or less, about every 5 centimeters or less, about every 4 centimeters or less, about every 3 centimeters or less, about every 2 centimeters or less, about every 1 centimeter or less, or any other suitable interval along at least a portion of or the entire length of the overlapping portion.

Figure 4:
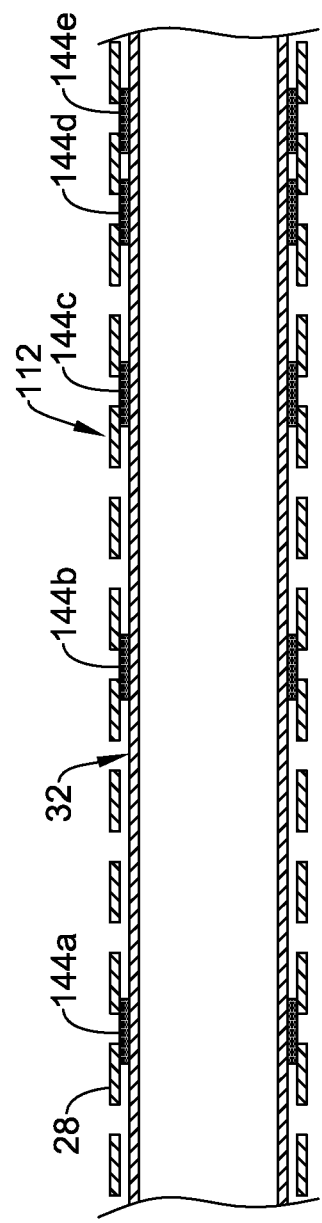
FIG. 4 is a longitudinal cross-sectional view of a portion of another example medical device.
Figure 5:
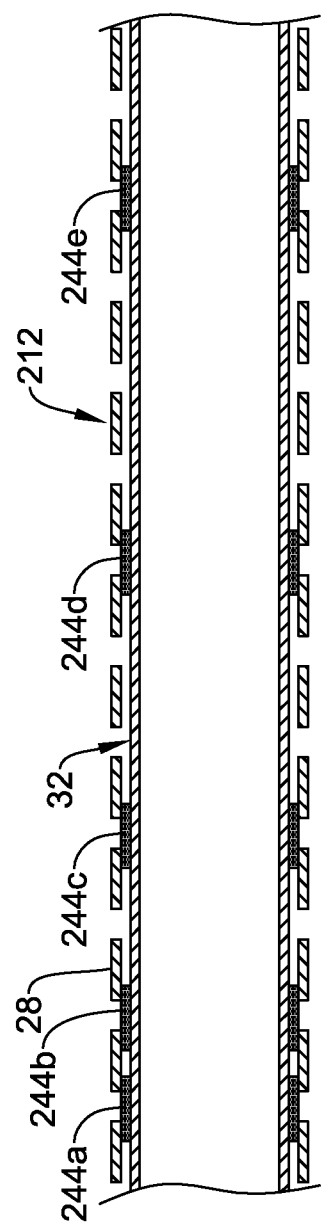
FIG. 5 is a longitudinal cross-sectional view of a portion of another example medical device.

In other embodiments, the interval can change along a portion or all of the length of liner 32. For example, FIGS. 4 and 5 illustrate alternative arrangements of bonding members wherein the number of bonding members changes per unit length of liner 32 along at least a portion of liner 32. For example, FIG. 4 illustrates another shaft 112, which may be similar in form and function to other shafts disclosed herein, where the number of bonding members 144a/144b/144c/144d/144e per unit length increases along the length of liner 32. This increase may occur in a regular, irregular, stepwise, or any other manner. Similarly, in FIG. 5 another shaft 212 is shown, which may be similar in form and function to other shafts disclosed herein, where the number of bonding members 244a/244b/244c/244d/244e per unit length decreases along the length of liner 32. It can be appreciated that other embodiments are contemplated where multiple changes in the number of bonding members per unit length occur along liner 32.

Figure 6:
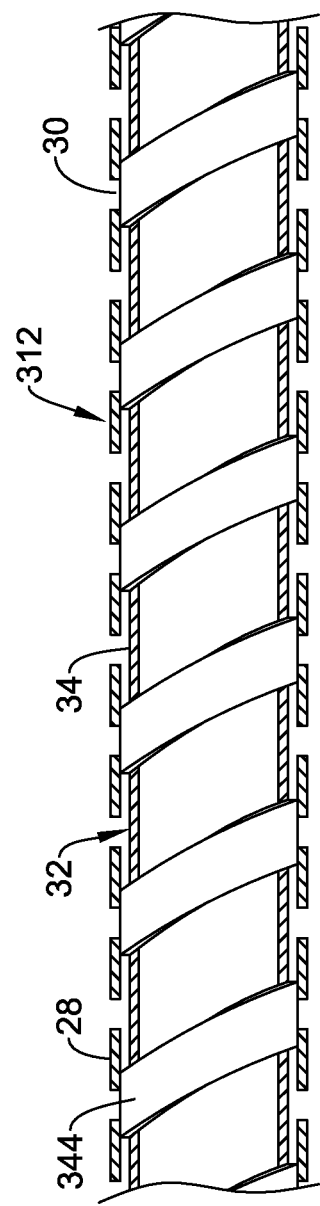
FIG. 6 is a partial cross-sectional view of a portion of another example medical device.

Turning now to FIG. 6, another shaft 312 is shown that may be similar in form and function to other shafts disclosed herein. In this embodiment, bonding member 344 follows a helical or spiral pattern along the outer surface 34 of liner 32. As is the case for any of the bonding member disclosed herein, bonding member 344 may take the form of a distinct structure element (e.g., a helical or spiral ribbon) or bonding member 344 may be a helical bonding pattern, configuration, or arrangement.

The direction or orientation of bonding member 344 may vary. For example, in some embodiments, bonding member 344 may be arranged so that it is angled in the same, consistent, direction. The direction may be either slanted toward the proximal end or the distal end of shaft 312. In other embodiments, the orientation of bonding member 344 may vary. For example, some portions may be angled (i.e., the pitch may be angled) toward the proximal end of shaft 312 while other portions may be angled toward the distal end. Furthermore, some embodiments may include some portions that are angled in the same direction but at a different angle. It can be appreciated that numerous variations in the arrangement of bonding member 344 are contemplated.

Bonding member 344 may have a width that may in the range of about 0.1 to 10 millimeters. For example, bonding member 344 may be about 5 millimeters or less in width. In addition, the pitch of bonding member 344 may be about 0.1 to 10 centimeters or about 0.5 to 5 centimeters. These dimensions are provided for illustration purpose and are not intended to be limiting.

As illustrated in FIG. 6, bonding member 344 may be continuous. For example, bonding member may follow an unbroken or continuous pattern about liner 34. The pattern may take the form of a helix or spiral. In some embodiments, the helix may have a constant pitch. In other embodiments, the pitch may vary along the length of bonding member 344. For example, bonding member 344 may include a first region having a first pitch and a second region having a second pitch different from the first pitch. Other variations in bonding member 344 are also contemplated. For example, some embodiments may include two or more helices. These embodiments may include a single, continuous bonding member 344 that extends in one direction and then loops back in the opposite direction to define two or more helices.

Alternatively, these embodiments may include a plurality of bonding members 344 that define a plurality of helices. The plurality of helices (i.e., the plurality of bonding members 344 defining the plurality of helices) may be oriented in the same or similar directions, in opposite directions, or in any suitable combination of directions. In still other embodiments, a plurality of bonding members 344 may be arranged so as to define one (e.g., a non-continuous, serial arrangement of bonding members 344 that, collectively, define a helix) or more helices.

In other embodiments, bonding member 344 may include several discrete bonding members that, collectively, follow a helical or spiral pattern about liner 34. For example, one or more bonding members 344 may be disposed at a first longitudinal position, a second set of one or more bonding member 344 may be disposed at an adjacent longitudinal position, etc. The second and subsequent sets of bonding members 344 may rotate about liner 34 such that bonding members 344 follow a helical pattern. In some embodiments, adjacent sets of bonding member 344 may be rotated at an angle relative to one another. For example, adjacent sets of bonding member 344 may be rotated more than about 90 degrees, about 90 degrees or less, about 85 degrees or less, about 80 degrees or less, about 75 degrees or less, about 70 degrees or less, about 65 degrees or less, about 60 degrees or less, about 55 degrees or less, about 50 degrees or less, about 45 degrees or less, or any other suitable angle. Essentially any other suitable angle or arrangement may be utilized without departing from the spirit of the invention.

The arrangement of bonding member 344 may be related to the arrangement of slots 30. For example, various embodiments of arrangements and configurations of slots 30 are contemplated. In some embodiments, at least some, if not all of slots 30 are disposed at the same or a similar angle with respect to the longitudinal axis of the tubular member 28. Slots 30 can be disposed at an angle that is perpendicular, or substantially perpendicular, and/or can be characterized as being disposed in a plane that is normal to the longitudinal axis of tubular member 28. However, in other embodiments, slots 30 can be disposed at an angle that is not perpendicular, and/or can be characterized as being disposed in a plane that is not normal to the longitudinal axis of tubular member 28. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 28 while still allowing for suitable torque transmission characteristics. Slots 30 may be formed such that one or more rings and/or turns interconnected by one or more segments and/or beams are formed in tubular member 28, and such rings and beams may include portions of tubular member 28 that remain after slots 30 are formed in the body of tubular member 28. Such an interconnected ring structure may act to maintain a relatively high degree of torsional stiffness, while maintaining a desired level of lateral flexibility. In some embodiments, some adjacent slots 30 can be formed such that they include portions that overlap with each other about the circumference of tubular member 28. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 28 to achieve desired properties. For example, adjacent slots 30, or groups of slots 30, can be arranged in a symmetrical pattern, such as being disposed essentially equally on opposite sides about the circumference of tubular member 28, or can be rotated by an angle relative to each other about the axis of tubular member 28. Additionally, adjacent slots 30, or groups of slots 30, may be equally spaced along the length of tubular member 28, or can be arranged in an increasing or decreasing density pattern, or can be arranged in a non-symmetric or irregular pattern. Other characteristics, such as slot size, slot shape and/or slot angle with respect to the longitudinal axis of tubular member 28, can also be varied along the length of tubular member 28 in order to vary the flexibility or other properties. In other embodiments, moreover, it is contemplated that the portions of the tubular member, such as a proximal section, or a distal section, or the entire tubular member 28, may not include any such slots 30.

As suggested above, slots 30 may be formed in groups of two, three, four, five, or more slots 30, which may be located at substantially the same location along the axis of tubular member 28. Within the groups of slots 30, there may be included slots 30 that are equal in size (i.e., span the same circumferential distance around tubular member 28). In some of these as well as other embodiments, at least some slots 30 in a group are unequal in size (i.e., span a different circumferential distance around tubular member 28). Longitudinally adjacent groups of slots 30 may have the same or different configurations. For example, some embodiments of tubular member 28 include slots 30 that are equal in size in a first group and then unequally sized in an adjacent group. It can be appreciated that in groups that have two slots 30 that are equal in size, the beams (i.e., the portion of tubular member 28 remaining after slots 30 are formed therein) are aligned with the center of tubular member 28. Conversely, in groups that have two slots 30 that are unequal in size, the beams are offset from the center of tubular member 28. Some embodiments of tubular member 28 include only slots 30 that are aligned with the center of tubular member 28, only slots 30 that are offset from the center of tubular member 28, or slots 30 that are aligned with the center of tubular member 28 in a first group and offset from the center of tubular member 28 in another group. The amount of offset may vary depending on the depth (or length) of slots 30 and can include essentially any suitable distance.

Slots 30 can be formed by methods such as micromachining, saw-cutting (e.g., using a diamond grit embedded semiconductor dicing blade), laser cutting, electron discharge machining, grinding, milling, casting, molding, chemically etching or treating, or other known methods, and the like. In some such embodiments, the structure of the tubular member 28 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. US 2003/0069522 and US 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing catheter 10 may include forming slots 30 in tubular member 28 using any of these or other manufacturing steps.

Numerous other arrangements are contemplated that take advantage of the various arrangements and/or configurations discussed above.

Referring back now to the arrangement of bonding member 344 relative to the arrangement of slots 30, slots 30 and/or the beams formed in tubular member 28 may follow a pattern about tubular member 28. For example, in some embodiments, the beams may follow a spiral or helical pattern about tubular member 28. In other embodiments, the beams may be longitudinally aligned, follow any other suitable pattern, or be disposed in any suitable arrangement.

Turning back now to FIG. 6 and turning also to FIGS. 6A and 6B, in some embodiments, bonding member 344 may follow, parallel, mimic, or otherwise be similar to a helical pattern followed by the beams. For example, both the groups of beams (e.g., the beams are labeled with reference number 31 in FIGS. 6A and 6B) and bonding member 344 may extend helically along the outer surface 34 of liner 32 in substantially the same direction (e.g., as depicted in FIG. 6 and FIG. 6A). In other embodiments, the beams and bonding member 344 may be oriented in different directions (e.g., as depicted in FIG. 6 and FIG. 6B). The bonding members of any of the other medical devices disclosed herein may also be related to the pattern of the beams.

With the above arrangements of various bonding members and the like in mind, it should be noted that any of the arrangements disclosed above can be combined with one another in various embodiments of catheters.

Other variations are contemplated for the various structures disclosed herein including suitable materials. Catheter 10 as well as the various components and variations thereof may include a number of different materials including metals, metal alloys, polymers (some examples of which are disclosed below), metal-polymer composites, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite\austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter 10, for example markers 26, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility is imparted into catheter 10. For example, to enhance compatibility with Magnetic Resonance Imaging (MRI) machines, it may be desirable to make all or portions of catheter 10, in a manner that would impart a degree of MRI compatibility. For example, tubular member 28 or portions thereof, or any other portion of catheter 10, may be made of a material that does not substantially distort the image and create substantial artifacts (artifacts are gaps in the image). Certain ferromagnetic materials, for example, may not be suitable because they may create artifacts in an MRI image. Tubular member 28 or portions thereof, or any other portion of catheter 10, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of catheter 10 that may define a generally smooth outer surface for catheter 10. In other embodiments, however, such a sheath or covering may be absent from a portion of all of catheter 10. The sheath may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

The sheath, if present, and/or liner 32 may be made from a lubricious, hydrophilic, protective, or other type of material. Alternatively, liner may include any other suitable material or combination of materials including any of those disclosed herein. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
an elongated tubular member having a length, an inner surface defining a lumen, a proximal end, and a distal end, the tubular member including a monolithic body having a length and including a plurality of slots formed therein;
a tubular liner disposed within the elongated tubular member, the liner having a length, an outer surface, and an inner surface defining a lumen, wherein the outer surface is spaced from the inner surface of the tubular member such that a space is defined therebetween;
a plurality of discrete bonding members disposed in the space and attaching the elongated tubular member to the tubular liner, wherein each of the plurality of bonding members is within 15 centimeters or less of an adjacent bonding member along the length of the tubular member;
wherein the plurality of discrete bonding members include a weld, adhesive bond, braze, crimp, solder bond, epoxy bond, bonding substance, thermal bond, or combinations thereof that fixedly attach the elongated tubular member to the tubular liner;
wherein a first group of bonding members are disposed along a first portion of the liner to provide the medical device with a first flexibility, the first group of bonding members including a pair of bonding members disposed opposite each other at a first longitudinal position along the liner and a second group of bonding members are disposed along a second portion of the liner, the second group of bonding members having a different number of bonding members from the first group of bonding members, the second group of bonding members including three or more bonding members that are equally spaced about the liner at a second longitudinal position along the liner different from the first longi- tudinal position so as to provide the medical device with a second flexibility different from the first flexibility; and wherein the number of bonding members per unit length decreases along the length of the liner and forms a smooth transition between the first flexibility and the second flexibility.

2. The medical device of claim 1, wherein the space has a volume and wherein the bonding members occupy 50% or less of the volume.

3. The medical device of claim 1, wherein the space has a volume and wherein the bonding members occupy 40% or less of the volume.

4. The medical device of claim 1, wherein the space has a volume and wherein the bonding members occupy 30% or less of the volume.

5. The medical device of claim 1, wherein the space has a volume and wherein the bonding members occupy 20% or less of the volume.

6. The medical device of claim 1, wherein the space has a volume and wherein the bonding members occupy 10% or less of the volume.

7. The medical device of claim 1, wherein at least a portion of the space remains unfilled by the bonding members.

8. The medical device of claim 1, wherein at least some of the bonding members extend circumferentially about the liner.

9. The medical device of claim 1, wherein at least some of the bonding members extend only partially circumferentially about the liner.

10. The medical device of claim 9, wherein two or more bonding members that extend only partially circumferentially about the liner are disposed at the same longitudinal position along the liner.

11. The medical device of claim 9, wherein the pair of bonding members of the first group of bonding members is defined by a pair of partially circumferential bonding members disposed opposite one another at the same longitudinal position along the liner.

12. The medical device of claim 11, wherein the three or more bonding members of the second group of bonding is defined by three or more partially circumferential bonding members disposed opposite one another at the same longitudinal position along the liner.

13. The medical device of claim 1, wherein at least one of the bonding members includes a bonding member that extends helically along the outer surface of the liner.

14. The medical device of claim 13, wherein groups of beams are defined in the tubular member between slots at the same longitudinal location, wherein the groups of beams follow a helical pattern about the tubular member, and wherein both the groups of beams and the bonding member that extends helically along the outer surface of the liner are oriented in substantially the same direction.

15. The medical device of claim 13, wherein groups of beams are defined in the tubular member between slots at the same longitudinal location, wherein the groups of beams follow a helical pattern about the tubular member, and wherein both the groups of beams and the bonding member that extends helically along the outer surface of the liner are oriented in different directions.

16. The medical device of claim 1, wherein each of the plurality of bonding members is within 10 centimeters or less of an adjacent bonding member along the length of the tubular member.

17. The medical device of claim 1, wherein each of the plurality of bonding members is within 5 centimeters or less of an adjacent bonding member along the length of the tubular member.

18. A medical device, comprising:

an elongated tubular member having an inner surface defining a lumen, a proximal end, and a distal end, the tubular member including a monolithic body having a length and including a plurality of slots formed therein;

a tubular liner disposed within at least a portion of the elongated tubular member such that the tubular member overlaps the liner along an overlapping portion having a length, the liner having an outer surface, and an inner surface defining a lumen, wherein the outer surface of the tubular liner is spaced from the inner surface of the elongated tubular member along the overlapping portion such that a space is defined therebetween; and a plurality of discrete, axially discontinuous bonding members disposed in the space and attaching the elongated tubular member to the tubular liner, wherein the plurality of bonding members are disposed such that there is at least one bonding member at intervals of 15 centimeters or less along the entire length of the overlapping portion;

wherein the plurality of discrete bonding members physically, chemically, or both physically and chemically bond the elongated tubular member to the tubular liner;

wherein at least some of the bonding members extend only partially circumferentially about the liner;

wherein a first group of bonding members is defined that includes two or more bonding members that extend only partially circumferentially about the liner and are disposed at the same longitudinal position along the length of the liner; and wherein the bonding members decrease in frequency along the length of the liner so as to define a smooth transition in flexibility of the medical device along the length of the liner.

19. The catheter of claim 18, wherein at least some of the bonding members extend circumferentially about the liner.

20. The catheter of claim 18, wherein a second group of bonding members is defined adjacent the first group that includes two or more bonding members that extend only partially circumferentially about the liner and are disposed at the same longitudinal position along the length of the liner, wherein the second group is rotated relative to the first group.

21. The catheter of claim 18, wherein the plurality of bonding members are disposed such that there is at least one bonding member at intervals of 10 centimeters or less along the entire length of the overlapping portion.

22. The catheter of claim 18, wherein the plurality of bonding members are disposed such that there is at least one bonding member at intervals of 5 centimeters or less along the entire length of the overlapping portion.

* * * * *